United States Patent [19]

Stach et al.

[11] 3,935,883

[45] Feb. 3, 1976

[54] SYRINGE FILLING APPARATUS WITH DISPOSABLE FLUID CONDUCTING ELEMENTS

[76] Inventors: Paul E. Stach, 4743 Glendon Road, Columbus, Ohio 43229; Thomas P. Sherrin, 1663 Dolliver Drive, Worthington, Ohio 43085

[22] Filed: Aug. 19, 1974

[21] Appl. No.: 498,456

[52] U.S. Cl. .................. 141/27; 141/94; 141/378; 128/214 R; 128/218 C; 23/259
[51] Int. Cl.² ........................................... B65B 3/04
[58] Field of Search ............ 141/27, 375, 279, 369, 141/267, 25, 26, 28, 114, 116, 378, 18, 1, 2, 94, 119; 222/181, 209; 206/46 FC; 248/206 A; 128/214, 218 C; 23/259

[56] References Cited
UNITED STATES PATENTS

| | | | |
|---|---|---|---|
| 3,182,692 | 5/1965 | Bittner | 141/25 |
| 3,197,285 | 7/1965 | Rosen | 141/25 |
| 3,292,667 | 12/1966 | Bittner et al. | 141/25 |
| 3,602,272 | 8/1971 | Stawski | 141/27 |
| 3,734,147 | 5/1973 | Borutta et al. | 141/27 |

*Primary Examiner*—Houston S. Bell, Jr.
*Attorney, Agent, or Firm*—Frank H. Foster

[57] ABSTRACT

An apparatus for the rapid, accurate and sterile filling of unit dosage, injection syringes with medication from a bulk source container or for reconstituting vials of drugs. A clamping means is mounted to a support frame for releasably retaining the outer cylinder member of a disposable, relatively large-volume, pumping syringe against all movement relative to the support frame. A gripper means for removable attachment to the piston member of the pumping syringe is mounted to the frame for linear reciprocation along the axis of the pumping syringe. A crank means, which has an adjustable offset for selecting dosage volume, is drivingly connected to a motor drive means and an associated connecting rod links the crank means to the gripper means for reciprocally driving the piston member of the pumping syringe. A disposable, dual check valve, tee connector is connected to a mating connector on the pumping syringe. It has an inlet connected to the bulk source container and an outlet port formed into a female Luer connector for receipt of the injection syringe or other male Luer connector. The motor drive means is energized by a control circuit for driving the crank through a single rotation to complete one pump cycle and fill the unit dosage syringe in response to a depression of the foot pedal actuating switch.

10 Claims, 8 Drawing Figures

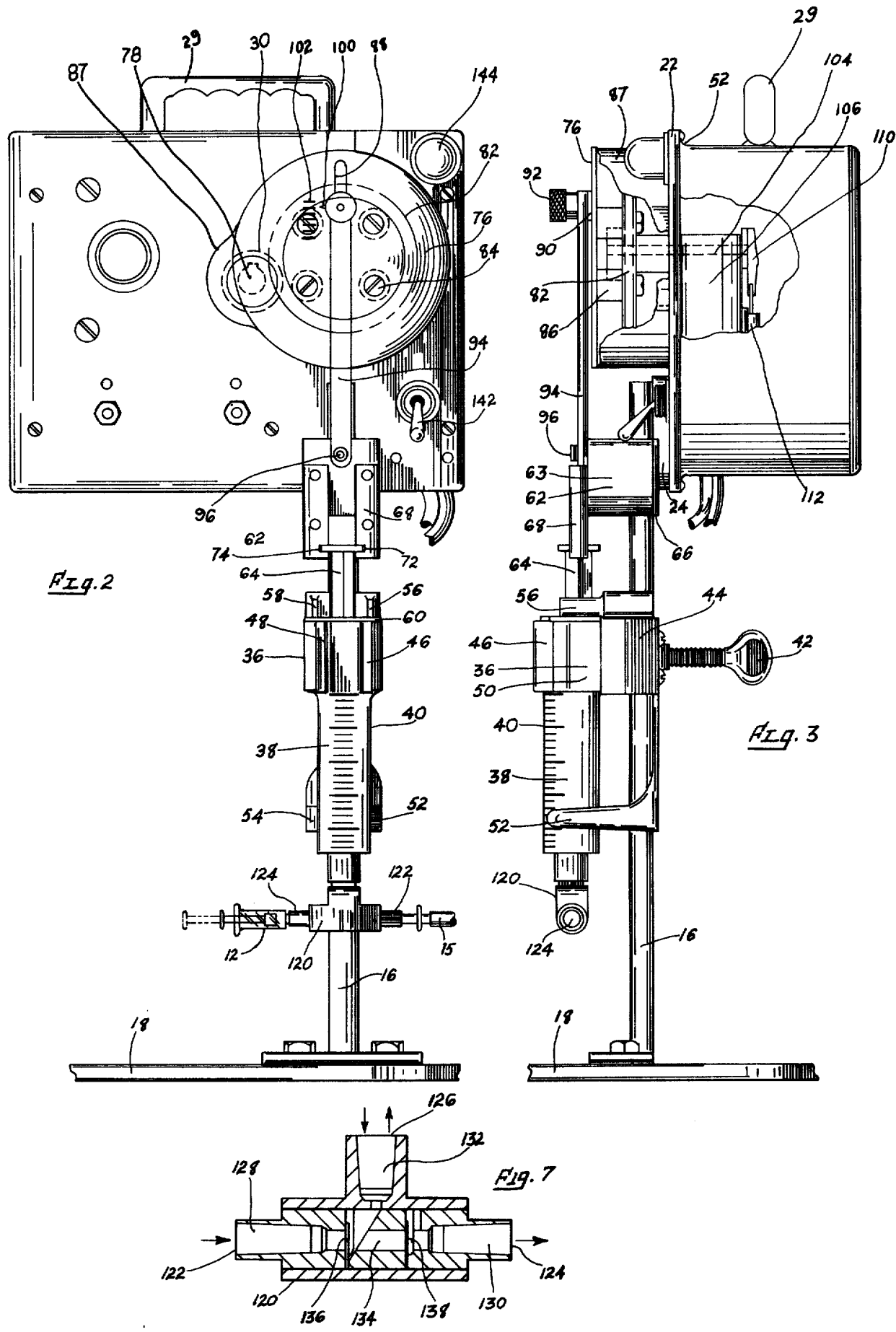

SYRINGE FILLING APPARATUS WITH DISPOSABLE FLUID CONDUCTING ELEMENTS

BACKGROUND OF THE INVENTION

The present invention relates generally to an apparatus for use in a pharmacy and more particularly relates to a device for more rapidly, safely and conveniently transferring unit dosages of a medical fluid from a bulk container to smaller containers such as vials or unit dosage syringes.

Those pharmacies which service relatively large hospitals are often required to fill many disposable unit dosage syringes with identical quantities of an identical medical fluid. For example, a large hospital may need, on a routine daily basis, 100 syringes each filled with 2 milliliters of a particular analgesic. Ordinarily, this work is performed in a laminar flow environment. It may be done entirely manually by piercing the needle of the unit dosage syringe through the resilient top of a vial and withdrawing the desired volume of the fluid.

Various other systems and associated apparatus have been devised for manually or semi-manually filling the dosage syringes. For example, a large syringe may be filled with the source fluid and used as the source. The smaller unit dosage syringes are consecutively connected in communication with the large syringe and manual depression of the plunger of the large syringe fills each smaller syringe. Other analogus hand pump systems have also been suggested.

The systems presently known suffer from one or more of several disadvantages. Those simple manual systems which require a minimum of equipment require tedious and extensive manual manipulation and depend upon a visual determination of the proper dosage volume. These systems are consequently very slow and require substantial human labor.

Those systems which utilize more elaborate mechanical equipment are often so bulky that they interrupt the laminar flow of the controlled environment so that it is no longer aseptic. Additionally and more importantly the fluid conducting elements of such equipment are designed for a unique mechanical function. They must be reused and require disassembly, thorough cleansing, sterilization and subsequent sterile reassembly. Some previously known mechanical devices expose the operator to dangerous moving mechanical parts. Some move or rock the syringe being filled making difficult the connection and disconnection of the syringe from the apparatus.

There is therefore a need for a compact apparatus for filling syringes and other relatively small medical fluid containers and which utilizes entirely disposable fluid conducting elements along its fluid path and which permits unit dosage syringes to be quickly, safely and easily connected to the apparatus, filled and then quickly disconnected to permit connection of the next syringe.

SUMMARY OF THE INVENTION

The invention is an apparatus for filling injection syringes with medical fluid from a source container and includes a support frame for positioning the apparatus in a suitable work area and a motor drive means mounted to the support frame. The apparatus has a clamping means mounted to the frame for releasably retaining the outer cylinder member of a pumping syringe against all movement relative to the frame. A gripper means for removable attachment to the piston member of the pumping syringe is mounted to the frame for linear reciprocation along the axis of the pumping syringe. A crank means is drivingly connected to the motor drive means and has an associated connecting rod linking the crank means to the gripper means for reciprocally driving the piston member. A dual check valve tee connector, which is connected to a mating connector on the pumping syringe permits fluid to be drawn into and expelled from the pumping syringe. The tee connector has an inlet port for connection to a source container to permit withdrawal of the fluid from the container into the pump syringe and also has an exhaust port formed into a female Luer connector for receipt of an injection syringe and permitting fluid flow from the pumping syringe to the injection syringe.

Accordingly, it is an object of the invention to provide an improved syringe filling device which enables syringes to be filled more easily, safely and rapidly.

Another object of the invention is to provide a syringe filling apparatus which permits a multiplicity of syringes to be more accurately filled.

Still another object of the present invention is to provide an apparatus and procedures for improving the sterility of a large number of prefilled syringes.

Yet another object of the present invention is to provide a syringe filling apparatus which may additionally be utilized for other pharmaceutical operations involving the transfer of fluids from bulk containers to smaller containers.

Further objects and features of the invention will be apparent from the following specification and claims when considered in connection with the accompanying drawings illustrating the preferred embodiment of the invention.

DESCRIPTION OF THE DRAWINGS

FIG. 2 is a view in front elevation of the preferred embodiment of the invention illustrated in FIG. 1.

FIG. 3 is a view in side elevation of the embodiment of the invention illustrated in FIG. 2.

FIG. 7 is a view in vertical section illustrating a dual check valve tee connector utilized in the preferred embodiment of the invention illustrated in FIG. 2.

Figure 1:
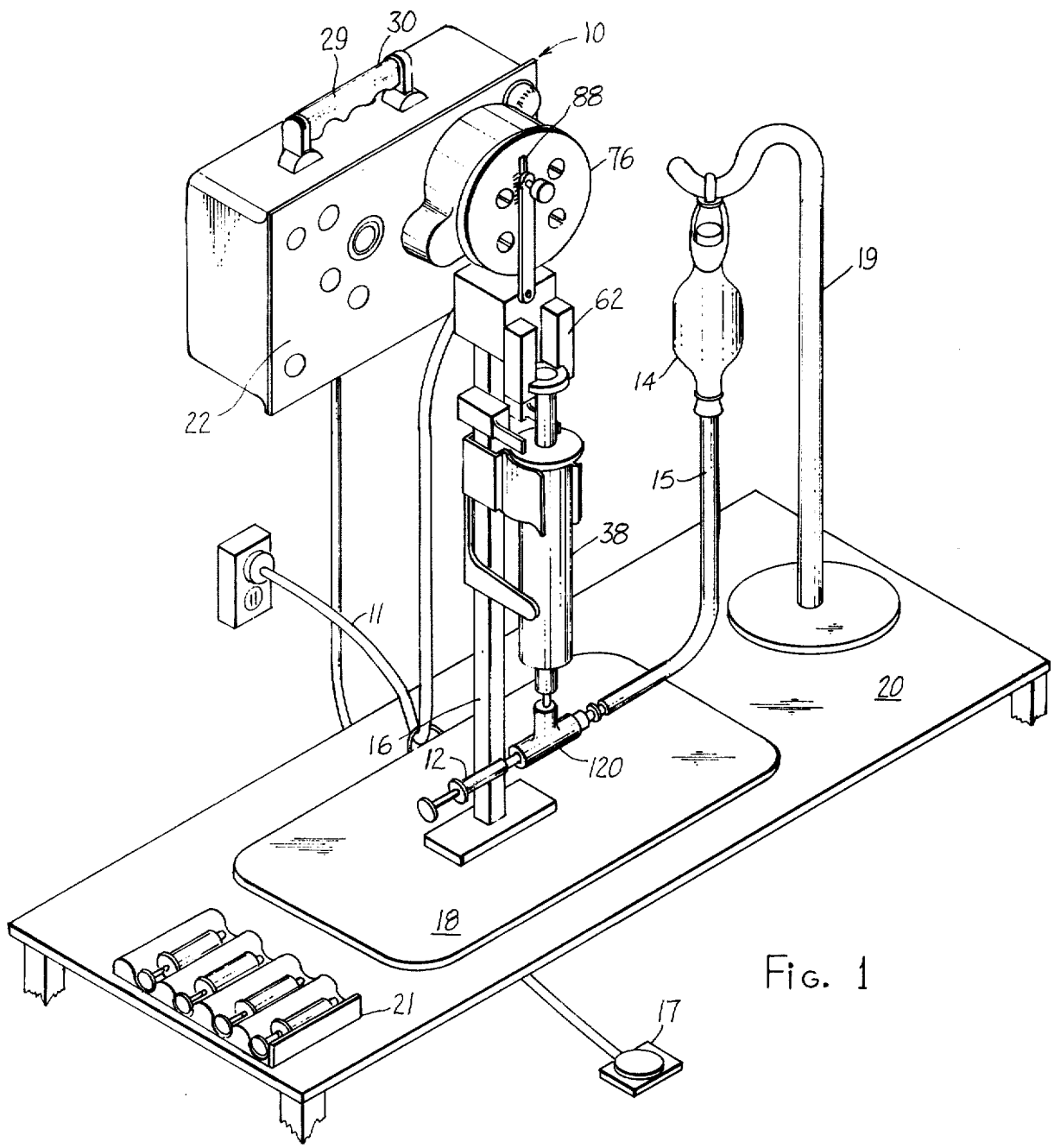
FIG. 1 is a view in perspective of the preferred embodiment of the invention shown being utilized for the filling of syringes.

In describing the preferred embodiment of the invention illustrated in the drawings, specific terminology will be resorted to for the sake of clarity. However, it is not intended to be limited to the specific terms so selected and it is to be understood that each specific term includes all technical equivalents which operate in a similar manner to accomplish a similar purpose.

DETAILED DESCRIPTION

FIG. 1 illustrates an apparatus 10 embodying the present invention which is manually actuated by a foot pedal 17 for use in filling an injection syringe 12 with a medical fluid from a source container 14 which is hanging upon a stand 19. Electrical power is supplied to the apparatus 10 by a power cord 11 which is fastened to the rear of the apparatus so that it will not interfere with the work of an operator.

Referring now to FIGS. 1–6, the preferred embodiment 10 of the invention has a support frame for positioning the apparatus in a suitable work area. The support frame includes a vertical bar 16 bolted at its lower end to a base plate 18 which forms a standard. Preferably, a plurality of rubber feet are mounted to the underside of the base plate 18 to provide a high friction, non-scratching material resting upon the work surface 20. A light may advantageously be mounted to the upper surface of the base plate 18 to back light the syringe being filled so that it may easily be inspected for possible visible contaminants. A vertically oriented mounting plate 22 is bolted or equivalently fixed to the rear of the upper end of the vertical bar 16 with an interposed spacer 24.

An electric motor drive means 26 having a speed reduction transmission 24 is mounted on the rearward surface of the mounting plate 22 and is enclosed by a louvered cabinet housing 30 screwed through its flanges 32 to the rear surface of the mounting plate 22. Preferably the electric motor is of the type which has an automatic brake which brakes the motor whenever the motor is not energized. A handle 29 is attached to the top of the cabinet housing 30 to facilitate carrying of the apparatus.

A clamping means 36 is slidably mounted to the vertical bar 16 for releasably retaining the outer cylinder member 38 of a relatively large pumping syringe 40 against all movement relative to the support frame. The clamping means 36 is slidably adjustable along the vertical bar 16 and releasably fixable in any position by tightening of a wing screw 42 against the rear surface of the vertical bar 16.

The clamping means also includes a pair of opposed, resiliently deflectable spring clips 44 having outwardly turned deflector guides 46 and 48 and cylindrically curved clamping portions, such as clamping portion 50 for conformingly seating against the outer surface of the pumping syringe 40.

A pair of lower retaining legs 52 and 54 extend forwardly on opposite sides of the pumping syringe 40 for supporting it against lateral movement. An upper pair of arms 56 and 58 extend forwardly immediately above the upper flange 60 of the cylinder member 38 of the pumping syringe 50 in order to retain the flange 60 between the spring clip 36 and the forwardly extending arms 56 and 58. This prevents vertical movement of the cylinder member 38 of the pumping syringe 40.

Thus, the upper arms 56 and 58, the spring clips and the lower arms 52 and 54 form a clamping means 36 which is vertically slidable as a unitary assembly along the vertical bar 16 so that the apparatus of the invention can accommodate pumping syringes of various heights.

A gripper means 62 is also slidable along the vertical bar 16 and is removably attached to the piston member 64 of the pumping syringe 40. The gripper means 62 is mounted for linear reciprocation along the axis of the pumping syringe 40 and preferably is formed by a block 63 of wear resistant, anti-friction nylon having a rectangular slot mating with the vertical bar 16 and retained in position by a back plate 66 fastened to the nylon block behind the vertical bar 16. Alternatively, the nylon block could have a back plate portion formed or molded as a unitary part of the nylon block itself.

A pair of vertically aligned, horizontally spaced arms 68 and 70 are fixed to the nylon block 63 and formed with a pair of inwardly facing horizontal slots 72 and 74 for removable receipt of the top of the piston member 64. These vertical arms 68 and 70 may alternatively be pivoted near their upper end and resiliently biased inwardly to accommodate a wider range of piston member sizes.

Thus, the clamping means 36 and the gripper means 64 are formed so that the entire pumping syringe 40 may be easily slid into position by a rearward horizontal movement of the syringe 40 into releasable engagement on the apparatus.

A rotatably driven disk 76 is drivingly connected to the output drive shaft 78 of the motor transmission 28 by means of meshing gears 80 and 82. The gear 82 is bolted to the circular disk 76 by means of four bolts, such as bolt 84, and interposed spacing tubes such as spacing tube 86. A forward protective housing 87 encircles the structures between the circular disk 76 and the mounting plate 22 and abuts the rear perimeter of the circular disk 76.

The circular disk 76 is formed with a radial slot 88 having a pivot block 90 releasably clamped in the slot 88. The pivot block 90 is releasable by unscrewing the knurled knob 92 and is formed with shoulders so that it travels along the slot 88 and may be releasably clamped in any selected position in the slot. A connecting rod 94 is pivotally connected at its upper end to the pivot block 90 and is pivotally connected to the gripper means 62 by a pivot pin 96 at its lower end.

Thus, the circular disk 76 and the adjustably slidable pivot block 90 together form a crank means which is driven by the motor means 26. This effective crank means is linked to the gripper means 62 by the associated connecting rod 94 for reciprocally driving the piston member 64 of the pumping syringe 40. However, because the pivot block 90 is releasably fixable at any selected position along the radial slot 88, the offset of the crank means may be adjustable for controlling the displacement of the pumping syringe 40.

To facilitate this adjustment, a pointer 100 is fixed to protrude laterally from the pivot block 90. It registers with an associated scale 102 etched or painted for example, upon the circular disk 76. Multiple scales may be provided on the circular disk 76 each corresponding to a pumping syringe of a different size.

The gear 82 and therefore the circular disk 76 are fixed to an axle 104 which rotates within a bearing 106 mounted to the rear of the mounting plate 22. Preferably, the axle 104, which forms the axis of rotation of the circular disk 76, is positioned immediately above the vertical bar 16 so that the gripper means 62 and the clamping means 36 are aligned and movable along a radius of the axis of rotation of the disk 76.

A cam 110 is fixed to the rearward end of the axle 104 and cooperates with a microswitch 112 to form a switch means in operative association with the effective crank means for sensing the particular position of the crank means which corresponds to the uppermost travel of the piston member 64 of the pumping syringe 40.

This switch means senses the uppermost angular position of the effective crank means and is connected to a control circuit for driving the motor drive means 26. As explained in more detail below, the control circuit operates, in a preferred mode of operation, so that the circular disk 76 and therefore the entire effective crank means will be driven through only one single rotation in response to one actuation of the foot pedal actuating switch 17.

A disposable, dual check valve, tee connector 120 is connected to a mating connector on the pumping syringe 40. This tee connector 120 has its check valves arranged to permit fluid to be drawn into the pumping syringe 40 during its upward intake stroke and expelled from the pumping syringe during its downward exhaust stroke. The tee connector 120 has an inlet port 122 with an associated check valve to permit the withdrawal of fluid through the tubing 15 from the source container 14 and into the pumping syringe 40 but block flow in the reverse direction. It is also provided with an exhaust port 124 which is formed into a female Luer connector for receipt of an injection syringe 12. This exhaust port 124 also has an associated check valve for permitting fluid flow from the pumping syringe 40 into the injection syringe 12 but blocking reverse flow.

Although many types of check valves are well known in the art and some disposable check valves are currently available, a particular check valve structure suitable for the present invention is illustrated in FIG. 7. This check valve has an inlet passage 128, an output passage 130 and a pumping syringe passage 132 in fluid communication with a central passage 134. An inlet diaphragm 136 permits fluid flow through the inlet passage and into the pumping syringe passage 132, but blocks fluid flow in the reverse direction. An outlet diaphragm 138 similarly permits fluid flow from the pumping syringe through the pumping syringe passage 132 and out the exhaust passage 130 but blocks flow in the reverse direction. Thus the partial vacuum produced by the intake stroke of the pumping syringe draws fluid into the inlet port 132 and into the pumping syringe while seating the outlet diaphragm 138 to prevent fluid passage through the outlet port 124. On the exhaust stroke the increased internal pressure relative to the atmosphere seats the diaphragm 136 to block passage out the intake port 122 while forcing fluid out the exhaust port 124.

As will become apparent in the discussion of the operation of the preferred embodiment of the invention, it is important that the outlet port of the tee connector be formed as a female Luer connector so that individual unit dosage injection syringes may be easily and directly connected to the tee connector 120. However, it should be appreciated that equivalent operation would occur if the tee connector were effectively extended through the use of flexible tubing to a more remote female Luer connector. However, such distance is generally undesirable.

Figure 8:
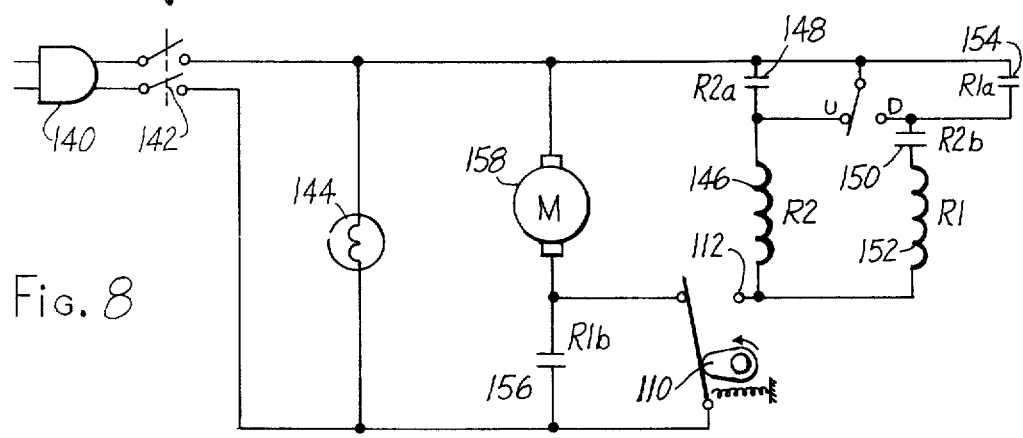
FIG. 8 is a schematic diagram of the control circuit for the preferred embodiment of the invention.
Figure 4:
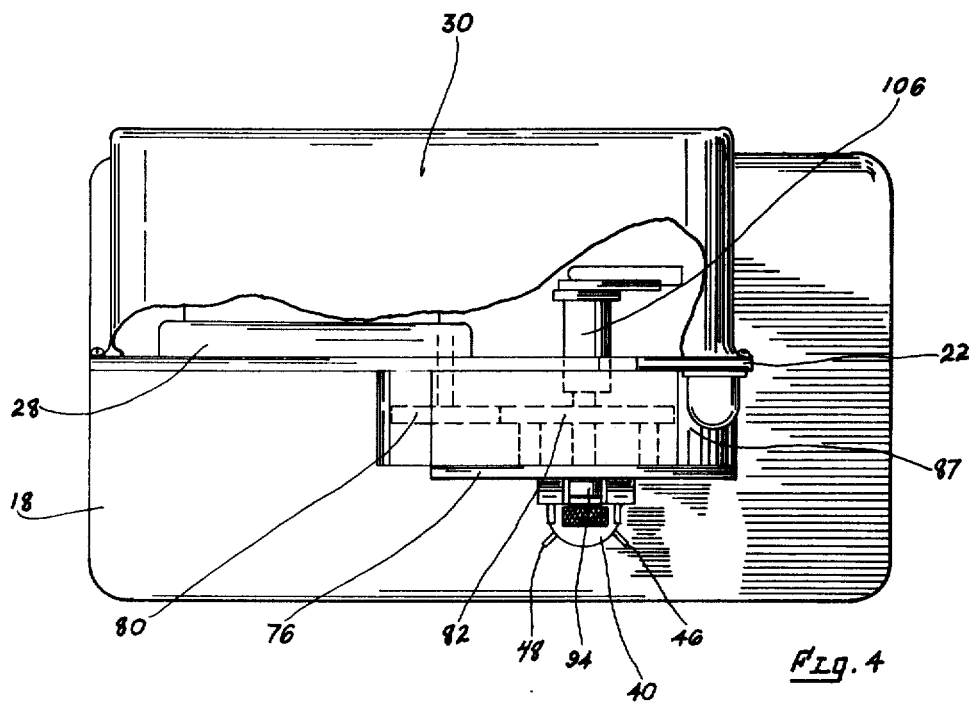
FIG. 4 is a top plan view of the embodiment of the invention illustrated in FIG. 2.
Figure 5:
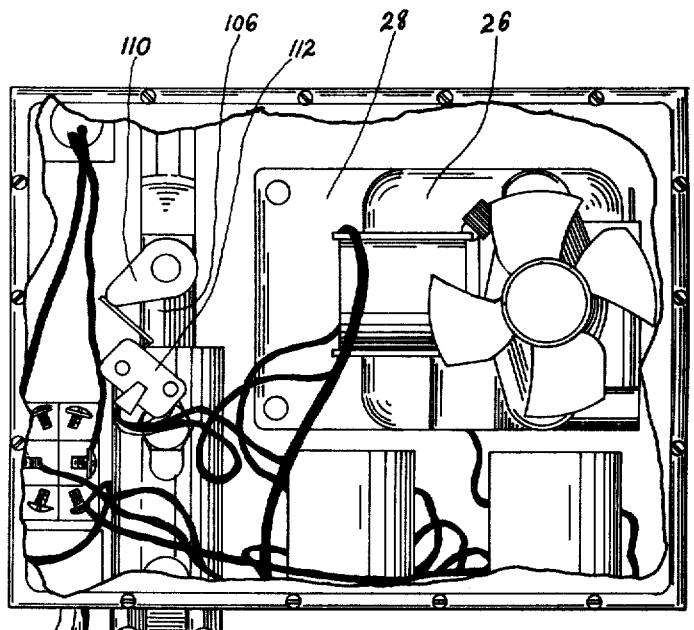
FIG. 5 is a rear view of the embodiment of the invention illustrated in FIG. 2 with a portion of the cabinet enclosure broken away to expose its interior mechanisms.
Figure 6:
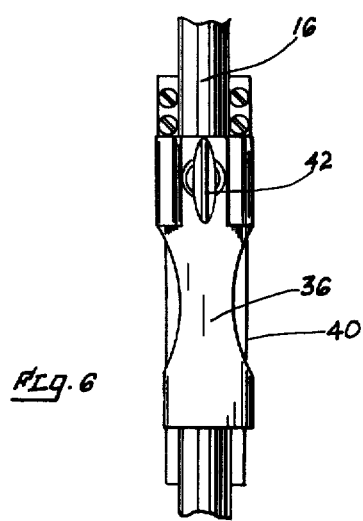
FIG. 6 is a rear view illustrating the detail of the clamping means portion of the embodiment of the invention illustrated in FIG. 2.

The illustrated embodiment of the invention is capable of various modes of cycling operation. For each mode, various control circuits can readily be designed by those skilled in the art. However, FIG. 8 illustrates one particular control circuit for a particular mode of operation. Power is supplied to the control circuit from a conventional male power connector 140 through an on/off double pole, single throw toggle switch 142 mounted to the mounting panel 22 of the preferred embodiment of the invention. With the switch 142 actuated, power is supplied to illuminate the pilot light 144 also mounted to the mounting panel 22.

When the toggle switch 142 is turned on and the circuit is energized the circuit will normally be in its static state with the foot pedal 17 in its up position U and the cam 110 just having released the single pole, double throw microswitch 112. In this static state, the relay coil 146 is energized and contacts 148 and 150 are closed. Contacts 148 are latching contacts to retain the relay coil 146 energized when the foot pedal actuating switch 17 is depressed to the position D. Upon such depression, relay coil 152 is energized and its latching contacts 154 are closed to retain it in a latched position even if the foot pedal is then released. The energization of relay coil 152 also closes contacts 156 to supply power to the motor 158 and begin rotation of the circular disk 176. A single pumping cycle is thus initiated.

Rotation of the disk will continue until the cam 110 engages the microswitch 112. This engagement switches the microswitch 112 which opens the circuit to relay coils 146 and 152. This open circuit in turn opens all relay contacts but power continues to be supplied to motor 158 through microswitch 112. However, the instant microswitch 112 is disengaged by cam 110, motor 158 is deenergized.

The embodiment of the invention is therefore preferably synchronized by angularly positioning the cam 110 on the axle 104 so that the cam disengages the microswitch 112 at the instant that the radial slot 188 is upwardly oriented.

The motor 158 will be deenergized and braked regardless of the position of the foot pedal actuation switch 117 because relay coils 146 and 152 are deenergized by the microswitch 112 upon contact thereof by the cam 110. Additionally, because relay contacts 150 are in series with relay coil 152, it is apparent that relay coil 146 must first be energized in order to enable the initiation of a subsequent cycle of operation. However, relay coil 146 can be energized only if the foot pedal actuating switch 117 is returned to its up position subsequent to release of the microswitch 112 by the cam 110.

The operation of the preferred embodiment of the invention begins with a determination by the pharmacist that a certain number of syringes need to be filled with an identical quantity of a particular medication for the use of the hospital during the coming days. The pharmacist withdraws a bulk container from a refrigerated or other suitable storage unit and brings it to the work surface 20. He then selects a suitable pumping syringe 40 which might, for example, be a 10 milliliter disposable syringe.

Next, a disposable dual check valve tee connector 120 is connected to the pumping syringe 40 and connected by suitable tubing 15 to the medical fluid source container 14 which is conveniently inverted upon the stand 19.

The pharmacist conveniently purges air bubbles from the fluid conducting path by holding the pumping syringe 40 in an inverted position, pulling the plunger to draw fluid into the pumping syringe 40 and then pushing the plunger into the syringe until all air is exhausted and a few drops of liquid are emitted from the tee connector 120.

The pumping syringe 40 while remaining connected to the bulk container 14 is installed in the clamping means by firmly pushing the syringe rearwardly between the spring clips 44 and sliding the top of the piston member 64 into the grooves 72 and 74. The wing screw 42 may be unscrewed so that the clamping means may be slid vertically to a position which permits the free movement of the piston member 64 and then retightened.

The knurled adjustment screw 92 may be loosened to permit the pivot block 90 to be slid along the radial slot 88 so that the desired unit dosage may be selected. The proper position may be selected by aligning the pointer 100 with the proper graduation on the scale 102. Alternatively, the graduations on the pumping syringe 40 may also be used to select the piston member displacement which gives the desired unit dosage. For example, the pivot block 90 may be moved until it is positioned coaxially with the axle 104 which forms the center of rotation of the circular disk 76. The reading then viewed on the graduations of the pumping syringe can be subtracted from a reading when the pivot block is offset from center. The difference is multiplied by two, to give the displacement for a single pump cycle.

After the desired dosage is chosen, the machine operator then may switch the toggle switch 142 to the on position. It is at this point that the operator may now begin filling a series of unit dosage syringes and that the remarkable advantages of the present invention become apparent. The operator positions a syringe 12 in communication with the fluid system by simply slidably inserting the male Luer connecting tip of the injection syringe 12 into the mating female Luer connector at the outlet port 124. The foot pedal actuating switch 17 is depressed and the apparatus of the present invention cycles and pumps the precise dosage of fluid into the injection syringe 12. At the completion of the cycle of apparatus automatically stops until the foot pedal actuating switch 17 is again depressed. The filled syringe 12 is moved and a sterile Luer tip cover is placed over the male Luer connector at the top of the syringe 12. Then the filled syringe 12 is replaced on a tray 21 and the next syringe is inserted. Thus, the operator may insert the syringe and depress the foot pedal actuating switch 17 and when the apparatus comes to rest remove the syringe and replace it with the next syringe. Each syringe may in turn be filled in this manner. All that is required is a simple insertion, foot pedal depression, removal and insertion of the next syringe.

Alternatively, the machine may be operated by a more skilled operator by observing that the fluid is pumped from the pumping syringe 40 into the unit dosage syringe 12 during the first half of the cycle. This occurs as the radial groove 88 moves from the upper vertical position to the lower vertical position. The second half of the cycle in which the piston member 64 is returned consists solely of drawing a new charge of fluid into the pumping syringe 40. Consequently, during this second half cycle the operator may withdraw the unit dosage syringe 12 and replace it with an empty syringe to be filled during the next cycle.

Other modes of operation also become readily apparent in view of the above disclosure. For example, it may that in some circumstances unit dosages are needed which are larger than the pumping syringe can deliver in a single cycle. For this purpose the circuitry may be modified by those skilled in the art so that multiple cycles of operation can be utilized for filling a unit dosage container. In this manner, the offset of the effective driving crank may be chosen so that the desired dosage is an integral multiple of the displacement of the pump syringe. The operator can therefore count the number of cycle of operation or alternatively suitable electronic circuitry can be utilized for counting and halting the continuous recycling after the selected number of cycles have occurred. The circuit may also be modified so that instead of cycling only once or a selected number of times for a single depression of the foot pedal actuating switch, it can be switched to operate continuously so long as the pedal is held depressed.

It is to be understood that while the detailed drawings and specific examples given describe preferred embodiments of the invention, they are for the purposes of illustration only that the apparatus of the invention is not limited to the precise details and conditions disclosed and that various changes may be made therein without departing from the spirit of the invention which is defined by the following claims.

I claim:

1. An apparatus for filling injection syringes with medical fluid from a source container and including a support frame for positioning said apparatus in a suitable work area and a motor drive means mounted to said frame, the apparatus comprising:
   a. a first pumping syringe;
   b. a clamping means mounted to said frame releasably retaining the outer cylinder member of said pumping syringe against all movement relative to said frame;
   c. gripper means for removable attachment to the piston member of said pumping syringe, said gripper means being mounted to said frame for linear reciprocation along the axis of said pumping syringe;
   d. crank means drivingly connected to said motor drive means and an associated connecting rod linking said crank means to said gripper means for reciprocally driving said piston member; and
   e. a dual check valve tee connector connected to a mating connector on said pumping syringe for permitting fluid to be drawn into and expelled from said pumping syringe, said tee connector having an input port for connection to said source container to permit the withdrawal of fluid from said container into said pumping syringe and also having an exhaust port formed into a female Luer connector for receipt of an injection syringe and permitting fluid flow from said pumping syringe to said injection syringe.

2. An apparatus according to claim 1 wherein said crank means includes adjusting means for varying the offset of said crank means for controlling the displacement of said pumping syringe.

3. An apparatus according to claim 2 wherein a pointer and scale means are associated with said adjusting means for indicating the displacement of said pump syringe.

4. An apparatus according to claim 1 wherein said motor drive means is energized by a control circuit including an actuating switch for driving said crank through only one single rotation in response to one actuation of said actuating switch and a switch means is provided in operative association with said crank means for sensing an angular position of said crank means.

5. An apparatus according to claim 1 wherein said crank means comprises a rotatably driven disk having a radial slot formed therein and having a pivot block travellable along and releasably clamped therein, said connecting rod being pivotally connected to said pivot block.

6. An apparatus according to claim 5 wherein said crank means, said gripper means and said pumping syringe clamping means are vertically aligned and wherein said clamping means is slidable adjustable and releasably fixable along the axis of alignment for accommodating pumping syringes of various heights.

7. An apparatus according to claim 6 wherein said support frame includes a vertical bar radially aligned with the axis of rotation of said crank means and wherein said gripper means and said clamping means are slidably mounted to said vertical bar.

8. An apparatus according to claim 7 wherein said support frame includes a base plate fastened to a lower end of said vertical bar and formed into a standard; wherein a switch means is provided in operative association with said crank means for sensing a position of said crank means and wherein said motor drive means is energized by a control circuit including an actuating switch and circuit means for driving said crank through only one single rotation in response to one actuation of said actuating switch; and wherein said motor drive means, said switch means and said control circuit are contained in a housing mounted to the upper end of said vertical bar.

9. An apparatus according to claim 8 wherein said switch means comprises a cam fixed relative to said crank for rotation therewith and a microswitch cooperatively associated with said cam for actuation thereby.

10. An apparatus according to claim 9 wherein said gripper means includes a pair of vertically aligned, horizontally spaced arms formed with inwardly facing slots for removable receipt of a plunger of the piston member of the pumping syringe.

* * * * *